US00PP18009P2

(12) United States Plant Patent
Egger

(10) Patent No.: US PP18,009 P2
(45) Date of Patent: Sep. 11, 2007

(54) *HEUCHERA* PLANT NAMED 'PEPPERMINT SPICE'

(50) Latin Name: ***Heuchera* hybrid**
Varietal Denomination: Peppermint Spice

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 29 days.

(21) Appl. No.: 11/385,345

(22) Filed: Mar. 20, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct hybrid of *Heuchera* plant characterized by medium size, white-veiled, red veined green leaves, showy pink flowers, a mounding habit and excellent vigor.

1 Drawing Sheet

Botanical denomination: *Heuchera* hybrid.
Variety designation: 'Peppermint Spice'.

BACKGROUND OF THE INVENTION

The present invention relates to a new and distinct cultivar of *Heuchera* and given the cultivar name of 'Peppermint Spice'. *Heuchera* is in the family Saxifragaceae. *Heuchera* 'Peppermint Spice' originated from a controlled cross between *Heuchera* 497-1-1 (an unpatented, proprietary plant) as the seed parent, and a massed population of unpatented, proprietary *Heuchera* 'Green Spice' hybrid as the pollen parent. This selection was made for its excellent foliage and flower form. Given its ornamental foliage and flower form, it is probable that *Heuchera sanguinea, H. americana, H. cylindrica,* and *H. micrantha* are in its parentage.

This new *Heuchera* is distinguished by:

1. White-veiled green leaves with red veins;
2. Showy pink flowers;
3. Once blooming;
4. Mounding habit;
5. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The drawing shows a one-year-old plant of *Heuchera* 'Peppermint Spice' growing in a one gallon container in the shade house in May in Canby, Oreg.

DETAILED PLANT DESCRIPTION

The following is a detailed description of the new *Heuchera* cultivar based on observations taken in May of a one-year-old specimen grown in a two gallon container in an open air shade house with 50% shade cover and added irrigation in the summer months in Canby, Oreg. Canby is Zone 8 on the USDA Hardiness map. Temperatures range from an average high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—17 cm tall from the ground to the top of the foliage and 26 cm wide.
*Habit.*—Mounding.
*Vigor.*—Excellent.
*Roots.*—Fibrous, freely branching, fine, and white in color; roots develop easily from tip cuttings.

Leaf:

*Type.*—Simple.
*Arrangement.*—Rosette.
*Shape.*—Broadly ovate.
*Lobing/division.*—5 main lobes, shallow and rounded, each notched 1 to 2 times.
*Venation.*—Palmate.
*Margins.*—Broadly crenate.
*Apex.*—Mucronulate.
*Base.*—Cordate, lobes usually overlapping at the base.
*Blade size.*—Usually about 11 cm long and 10 cm wide.
*Surface texture.*—Top surface is glabrous; bottom has very short glands along main veins.
*Petiole description.*—9 to 12 cm long and 2 mm wide with the surface having very short glandular hairs, color is Green 148A.
*Leaf color.*—Top side — Yellow Green 147B on the leaf edges and on leaf veins of older leaves with an overlay closest Greyed Green 198D on the rest of the leaf; leaf veins are Greyed Purple 183A. Bottom side — Yellow Green 147B.

Inflorescence:

*Type.*—Thyrse.

*Number of flowers.*—About 60 per thyrse.

*Number of thyrse in spring.*—5.

*Peduncle.*—With 0 to 1 cauline leaf, 40 cm tall and 2.5 mm wide at the base, Greyed Orange 165A, with glandular hairs.

*Pedicel.*—Variable in length, Greyed Orange 165A, with glandular hairs.

*Bloom period.*—May to mid June.

Flower bud:

*Size.*—3 mm wide and 5 mm long.

*Description.*—Glandular, ovoid, down facing.

*Color.*—Red Purple 62D on the bottom half and Red Purple 62C on the top half.

Flower:

*Type.*—Perfect, zygomorphic.

*Shape.*—Campanulate.

*Size.*—6 mm long and 6 mm wide.

*Corolla description.*—5 petals, each obovate with a clawed base, tip acute, margin entire to two notched, glandular hairs, 3 mm long and 1.5 mm wide, light pink in color, Red Purple 62C on both sides.

*Calyx description.*—Campanulate, 5 lobes, spreading open, divided ½ way to the base, glandular on both sides, tips acute, margin entire, 6 mm long and 6 mm wide.

*Calyx and overall flower color.*—Inside: Red Purple 69C on tube to Red Purple 62B on lobe tips. Outside: Red Purple 63C on base to 69A in middle and 62B on lobes. Past maturity: Red Purple 63C.

*Stamen description.*—5 in number, filaments 1 mm long, White 155D, anthers sterile, no pollen produced, oval and about 0.5 mm long, Red Purple 59A.

*Pistil description.*—6 mm long, stigma and style are White 155B, stigma is 2 parted, ovary is Yellow Green 145C.

*Fragrance.*—None.

*Lastingness.*—Each thyrse blooms for about 3 weeks on the plant.

Fruit:

*Type.*—Two-beaked ovoid capsule.

*Color.*—Brown 200D.

Seed:

*Shape.*—Linear.

*Size.*—2 mm long.

*Color.*—Black 202A.

Pest and disease tolerance: This new *Heuchera* has not proved to be resistant to pathogens or pests common to *Heuchera.*

COMPARISON TO SIMILAR *HEUCHERA*

Compared to *Heuchera americana* 'Green Space', an unpatented plant, this new *Heuchera* has flowering stems that are much shorter, having 0 to 1 cauline leaf rather than multiple leaves, and have flowers that are showy and pink rather than small and yellow green.

Compared to *Heuchera* 497-1-1 (unpatented, proprietary plant) this new *Heuchera* differs primarily in flower color.

Compared to *Heuchera* 'Strawberry Candy' (U.S. Plant Pat. No. 12,195), this new variety is much larger overall. It has larger leaves with more distinct white veiling and reddish veins rather than green veins.

I claim:

1. A new and distinct hybrid of *Heuchera* plant as herein illustrated and described.

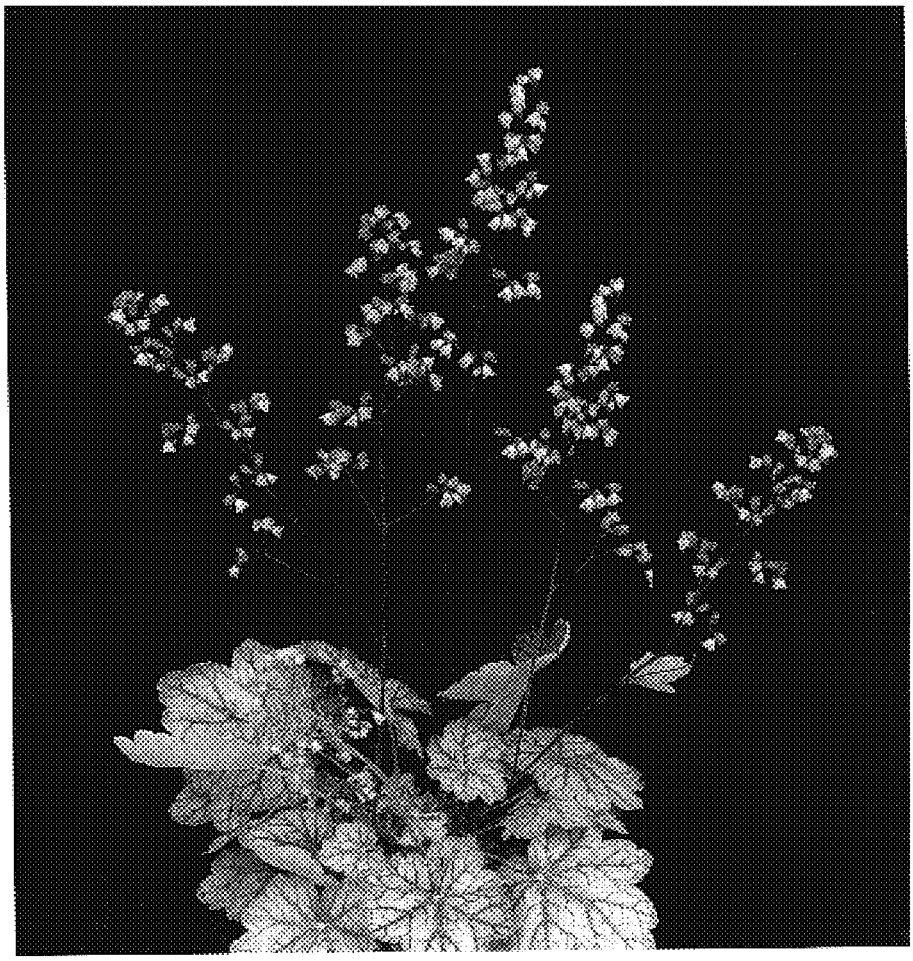

* * * * *